United States Patent [19]

Claussner et al.

[11] Patent Number: 5,202,316

[45] Date of Patent: Apr. 13, 1993

[54] N,N,N',N'-6-(1-PIPERAZINYL)-2,5-PYRIDINEDIAMINES

[75] Inventors: André Claussner, Villemomble; Jacques Leclaire, Massy; Lucien Nedelec, le Raincy; Daniel Philibert, la Varenne Saint Hilaire, all of France

[73] Assignee: Roussel Uclaf, Paris, France

[21] Appl. No.: 774,568

[22] Filed: Oct. 9, 1991

Related U.S. Application Data

[63] Continuation of Ser. No. 497,563, Mar. 21, 1990, abandoned.

[30] Foreign Application Priority Data

Mar. 22, 1989 [FR] France ................ 89 03740

[51] Int. Cl.$^5$ ............... A61K 31/58; C07J 43/00; C07D 401/02
[52] U.S. Cl. ................ 514/176; 514/252; 540/107; 540/109; 540/111; 544/360; 544/364
[58] Field of Search ............... 544/360, 364; 514/252, 514/176; 540/107, 109, 111

[56] References Cited

U.S. PATENT DOCUMENTS

| | | | |
|---|---|---|---|
| 4,189,431 | 2/1980 | Johnson et al. | 549/221 |
| 4,565,656 | 1/1986 | Nedelec et al. | 540/36 |
| 4,996,318 | 2/1991 | Gall et al. | 544/360 |
| 5,099,019 | 3/1992 | McCall et al. | 544/295 |

FOREIGN PATENT DOCUMENTS

| | | |
|---|---|---|
| 263213 | 4/1988 | European Pat. Off. . |
| 8701706 | 3/1987 | World Int. Prop. O. . |

OTHER PUBLICATIONS

Muray et al., Chem. Abst. 48-11504b (1954) Abstract of U.S. Pat. No. 2,656,370.
Babcock et al., Chem. Abst. vol. 51, 6712g (1957) Abstract of U.S. Pat. No. 2,775,602.
Herr, Chem. Abst. vol. 52, 1298d (1958) Abstract of U.S. Pat. No. 2,793,218.
Nedelec et al., Chem. Abst. 95-98147n (1981).
Braughleit et al., Journal of Biological Chem. 262(22) pp. 10438-10440 (1987).
McCall et al., Chem. Abst. 111-78020m (1989).
Jacobsen et al., Journal of Medicinal Chem. vol. 33, pp. 1145-1151 (1990).

Primary Examiner—Cecilia Tsang
Attorney, Agent, or Firm—Bierman & Muserlian

[57] ABSTRACT

A compound selected from the group consisting of a compound of the formula

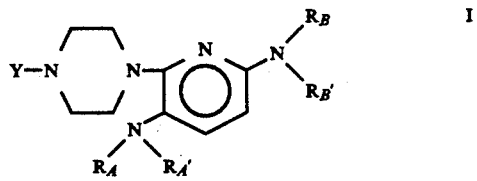

wherein $R_A$, $R'_A$, $R_B$ and $R'_B$ are individually selected from the group consisting of hydrogen and alkyl of 1 to 4 carbon atoms or $R_A$ and $R'_A$ or $R_B$ and $R'_B$ together with the nitrogen atom to which they are attached form a 5- to 6-member heterocycle optionally substituted with alkyl of 1 to 3 carbon atoms and Y is hydrogen or

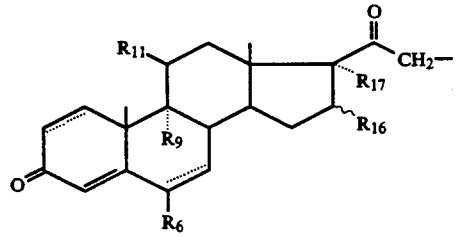

wherein $R_6$ is selected from the group consisting of hydrogen, —$CH_3$, —F and —Cl, $R_9$ and $R_{11}$ form a second bond at 9(11) or $R_9$ is hydrogen or —F is hydrogen, —OH or =O, $R_{16}$ is —$CH_3$ or hydrogen, $R_{17}$ is hydrogen, —OH or acyloxy, the dotted lines indicate the possible presence of a second bond at 1(2) and 6(7)-positions and the wavy line indicates the α- and β-position and their non-toxic, pharmaceutically acceptable acid addition salts having anti-inflammatory and antioxidant activity.

29 Claims, No Drawings

N,N,N',N'-6-(1-PIPERAZINYL)-2,5-PYRIDINEDIAMINES

This is a continuation of Ser. No. 497,563 filed Mar. 21, 1990, now abandoned.

Related prior art includes PCT patent application Nos. WO.A. 8,701,706 and WO.A 8,707,895.

OBJECTS OF THE INVENTION

It is an object of the invention to provide the novel compounds of formula I and their non-toxic, pharmaceutically acceptable acid addition salts and a novel process and novel intermediates for their preparation.

It is another object of the invention to provide novel anti-inflammatory compositions and a method of treating inflammation in warm-blooded animals.

These and other objects and advantages of the invention will become obvious from the following detailed description.

THE INVENTION

The novel compounds of the invention are selected from the group consisting of a compound of the formula

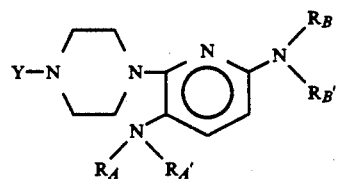

wherein $R_A$, $R_A'$, $R_B$ and $R_B'$ are individually selected from the group consisting of hydrogen and alkyl of 1 to 4 carbon atoms and/or $R_A$ and $R_A'$ or $R_B$ and $R_B'$ together with the nitrogen atom to which they are attached form a 5- to 6-member heterocycle optionally substituted with alkyl of 1 to 3 carbon atoms and Y is hydrogen or

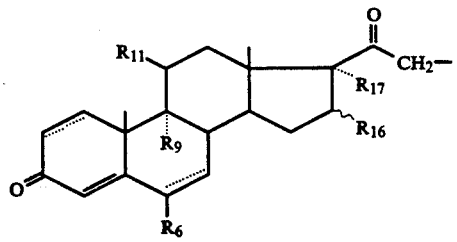

wherein $R_6$ is selected from the group consisting of hydrogen, —$CH_3$, —F and —Cl, $R_9$ and $R_{11}$ form a second bond at 9(11) or $R_9$ is hydrogen or —F and $R_{11}$ is hydrogen, —OH or =O, $R_{16}$ is —$CH_3$ or hydrogen, $R_{17}$ is hydrogen, —OH or acyloxy, the dotted lines indicate the possible presence of a second bond at 1(2) and 6(7)-positions and the wavy line indicates the α- and β-position and their non-toxic, pharmaceutically acceptable acid addition salts.

Examples of $R_{17}$ wherein it is acyloxy are acetyloxy, propionyloxy and benzoyloxy and examples of alkyl for $R_A$, $R_A'$, $R_B$ and $R_B'$ are methyl, ethyl, n-propyl, isopropyle, n-butyl, tert.-butyl, isobutyl, sec-butyl and preferably methyl or ethyl.

When $R_A$ and $R_A'$ and/or $R_B$ and $R_B'$ with the nitrogen atom to which they are attached form a heterocycle, the latter is a saturated heterocycle, preferably pyrrolidine or piperidine optionally substituted with alkyl such as methyl, ethyl, propyl or isopropyl, and more preferably methyl or ethyl, or an unsaturated heterocycle, preferably pyrrole optionally substituted with alkyl such as methyl.

Examples of suitable acids to form the non-toxic, pharmaceutically acceptable acid addition salts are inorganic acids such as hydrochloric acid, hydrobromic acid, nitric acid, sulfuric acid, phosphoric acid, organic acids such as acetic acid, formic acid, propionic acid, maleic acid, fumaric acid, succinic acid, tartaric acid, citric acid, oxalic acid, glyoxylic acid, and aspartic acid, alkanesulfonic acids such as methane- or ethanesulfonic acid, arylsulfonic acids such as benzene- or p-toluenesulfonic acids and arylcarboxylic acids such as benzoic acid.

Among the preferred compounds of the invention are those of the formula

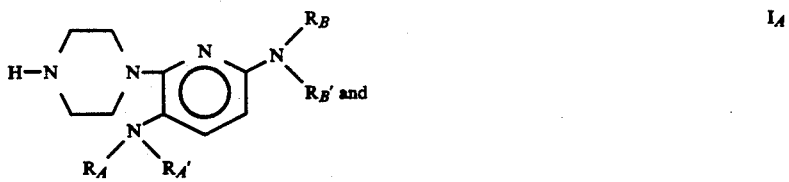

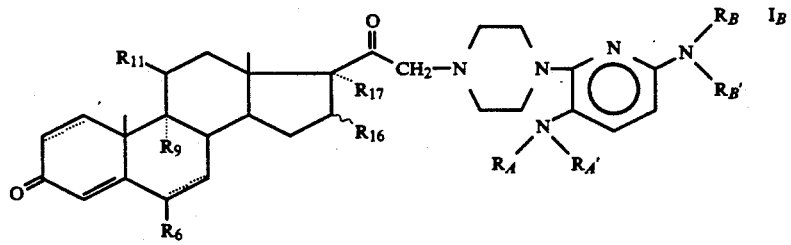

wherein $R_6$, $R_9$, $R_{11}$, $R_{16}$, $R_{17}$, $R_A$, $R_A'$, $R_B$ and $R_B'$, the dotted lines and the wavy line have the above meanings.

Among the preferred compounds of formula $I_B$ are those wherein $R_6$ is hydrogen, those wherein $R_9$ and $R_{11}$ form a second bond in the 9(11)-position, those wherein $R_{16}$ is α-methyl, those wherein $R_{17}$ is hydrogen and those wherein the dotted line in the 1(2)-position is a second bond and their acid addition salts.

Specific preferred compounds of the invention are N,N,N',N'-tetraethyl-6-(1-piperazinyl)-2,5-pyridinediamine and 21-(4-[3,6-bis(diethylamino)-2-pyridyl]-1-piperazinyl)-16α-methyl-$\Delta^{1,4,9(11)}$-pregnatriene-3,20-dione and their salts.

The novel process of the invention for the preparation of the compounds of formula I comprises reacting a compound of the formula

in which R' is an amino protecting group with a product of the formula

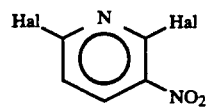

in which Hal is halogen to obtain a product of the formula

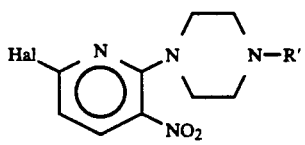

reacting the latter with a product of the formula

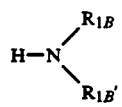

in which $R_{1B}$ and $R_{1B}'$ have the meanings for $R_B$ and $R_{B'}$, or are such that one is a monovalent group amino protecting function and the other is hydrogen, or $R_{1B}$ and $R_{1B}'$ together are a divalent amino protective group to obtain a product of the formula

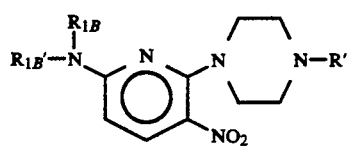

subjecting the latter to a hydrogenation to obtain a product of the formula

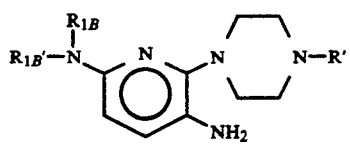

optionally a) subjecting the latter to the action of one or two equivalents of a monohalogenated derivative of $R_A$ or of $R_A'$ to obtain a product of the formula

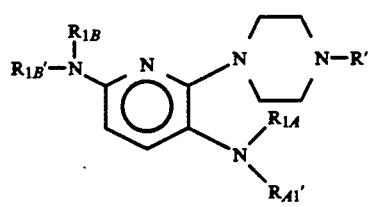

in which either one of $R_{A1}$ and $R_{A1}'$, is hydrogen and the other is alkyl, or both $R_{A1}$ and $R_{A1}'$ are the same alkyl or b) subjecting the compound of formula VII to the action of a monohalogenated derivative of $R_A$ or of $R_A'$, and then to the action of a monohalogenated derivative of $R_A'$ or of $R_A$ to obtain a product of the formula

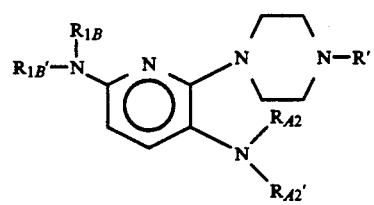

in which $R_{A2}$ and $R_{A2}'$ are different alkyls or c) subjecting the compound of formula VII to the action of a dihalogenated derivative of butane or pentane optionally substituted with an alkyl of 1 to 3 carbon atoms to obtain a product of the formula

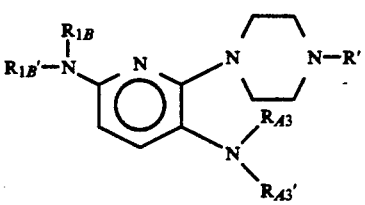

in which $R_{A3}$ and $R_{A3}$, form with the atom to which they are attached a 5- or 6-membered heterocycle, the products of formulae VII, VII', VII'' and VII''' being subjected to a reaction of unblocking of the group R' and, if desired, of the groups $R_{1B}$ and/or $R_{1B}'$ to obtain a compound of the formula

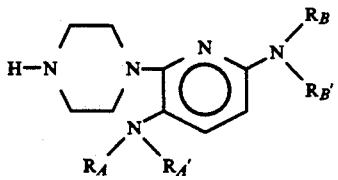

in which $R_A$, $R_A'$, $R_B$ and $R_B'$ have the above meanings, optionally salifying the product of formula $I_A$, or optionally subjecting the same in a neutral solvent and in the presence of a base to the action of a compound of the formula

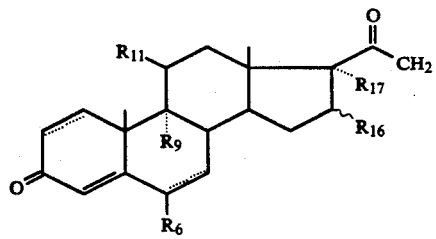

in which X is halogen and $R_6$, $R_9$, $R_{11}$, $R_{16}$, $R_{17}$, the dotted lines and the wavy line have the same above meanings to obtain a compound of the formula

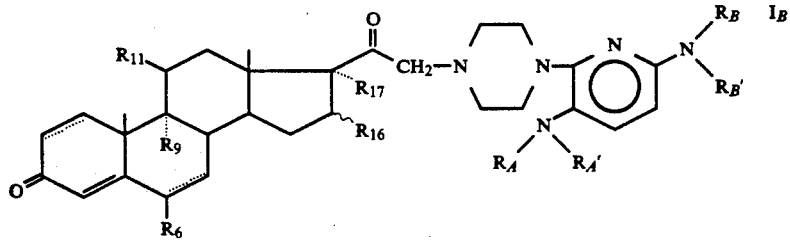

and optionally subjecting the latter to the action of an acid to obtain the corresponding salt.

In a preferred embodiment of the process of the invention, the compounds of formula $I_A$ are obtained by reacting a product of formula II in which the group protecting the amino function is, for example, acetyl with a product of formula III in which Hal is, for example, chlorine. In the product of formula V, the monovalent group protecting the amino function of $R_{1B}$ or $R_{1B}'$ is, for example, benzyl or trityl and when $R_{1B}$ and $R_{1B}'$ together are a divalent group, they can, for example, form together with the nitrogen atom to which they are attached 2,5-dimethylpyrrole.

The compounds of formula $I_B$ are obtained by reacting a compound of formula VIII in which X is chlorine, bromine or iodine in a neutral solvent such as dimethylformamide, tetrahydrofuran, methylene chloride, acetonitrile, ethyl ether or acetone in the presence of a base such as an alkali metal carbonate or bicarbonate, preferably sodium or potassium carbonate or bicarbonate, triethylamine or diisopropylethylamine with the N-substituted piperazine of formula $I_A$.

In a preferred embodiment of the process of the invention the compound of formula VIII is 21-iodo-16α-methyl-$\Delta^{1,4,9(11)}$-pregnatriene-3,20-dione of Patent Application No. WO 8,701,706 and the neutral solvent is acetone and the base is potassium carbonate.

The compounds of formula I may be obtained in the form of acid addition salts by known methods which consist in reacting the compound of formula I with an inorganic or organic acid selected from the list of acids shown above. Preferred acids of the invention are methanesulfonic acid or fumaric acid.

The anti-inflammatory compositions of the invention are comprised of an anti-inflammatorily effective amount of at least one compound of formula I and its non-toxic, pharmaceutically acceptable acid addition salts and an inert pharmaceutical carrier. The compositions may be in the form of tablets, dragees, capsules, granules, creams, pomades, suppositories or injectable solutions or suspensions.

Examples of suitable excipients are talc, starch, aqueous or non-aqueous vehicles, fats of animal or vegetable origin, paraffin derivatives, glycols, the various wetting, dispersant or emulsifying agents and preservatives.

The compositions may be used in the treatment of inflammatory reactions such as the treatment of local inflammatory reactions such as oedema, dermatoses, pruritus, the various forms of eczema and solar erythema, or for the treatment of acute inflammatory diseases or chronic inflammatory diseases, for example rheumatoid arthritis, psoriasis or multiple sclerosis.

The compositions of the invention also have an antioxidant activity by inhibition of tissue lipid peroxidation, for example in the kidney and heart and especially in the brain and spinal cord. The compositions also display a detoxifying activity in acute intoxications associated with the peroxidation of lipids of brain tissues such as the brain or spinal cord as well as an advantageous anti-inflammatory activity, for example in the phenomena of acute inflammation mediated by arachidonic acid derivatives.

The compositions may be used in the treatment of biological disorders following trauma. Trauma is understood to mean tissue damage in which the generation of lipid peroxides is involved, and which may be produced by a variety of agents, for example physical agents such as contusions, especially cerebral contusions associated or otherwise with local haemorrhage, or chemical agents such as those used in antitumor chemotherapy, for example adriamycin, or such as those used in cancer immunotherapy, for example IL-2 or TNF. They are most especially advantageous in the treatment of cerebral ischaemia, especially in the treatment of cerebral infarction and in the prevention of its recurrence, or in the treatment of drug intoxication produced by chemotherapy or immunotherapy or a combination of the two.

The novel method of treating inflammation in warm-blooded animals, including humans, comprises administering to warm-blooded animals an anti-inflammatorily effective amount of at least one compound of formula I and its salts. The compounds may be administered orally, parenterally such as by intramuscular, intra-articular or intrathecal injection, and preferably by intravenous injection in a bolus or in continuous perfusion, or locally by topical application to the skin or the mucosae. The usual daily dose is 0.01 to 1 mg/kg depending on the condition treated, the method of administration and the specific compound. The more water-soluble salts are preferably used for aqueous formulations for intravenous administration.

The compounds of Formula VIII used in the process of the invention are 21-halo steroids which may be prepared generally, from the corresponding 21-hydroxylated steroids by methods known to those skilled in the art, or, for example, according to the process described in Patent Application WO 8,701,706.

21-hydroxylated steroids having a 17α-hydrogen or a hydroxyl are known steroids or steroids whose preparation is known to those skilled in the art. They can be prepared from the corresponding 17-keto steroids using the processes described in the French Patent Applications No. 2,462,445 and No. 2,498,607. The 17-keto steroids are themselves known products described in U.S. Pat. Nos. 2,775,602; 2,793,218; 4,189,431; 3,505,365 or 2,656,370.

Steroids having an 17α-acyloxy are prepared by acylation of the corresponding 17α-hydroxylated steroids Steroids having a double bond at position 9(11) are known products or products prepared by methods known to those skilled in the art, for example by dehydration of a corresponding 11-hydroxylated steroids with a mixture of methanesulfonyl chloride and thionyl chloride.

Steroids having a 1(2) or 6(7) double bond are obtained from the corresponding Δ$^4$ derivative by methods known to those skilled in the art, for example by the action of a p-benzoquinone derivative such as chloranil or 2,3-dichloro-5,6-dicyanobenzoquinone (DDQ). Derivatives having a 1(2) double bond may also be obtained biochemically with microorganisms such as Arthrobacter simplex.

Steroids having a 6-methyl radical are prepared by methods known to those skilled in the art, for example by the action of a methylmagnesium halide on a corresponding 5(6)-epoxy steroid having a 3-ketone blocked, for example, by an acetal group. Steroids having a 6-fluorine atom are prepared by known methods, for example by addition of the hydrofluoric acid/dimethylformamide complex to a corresponding 5(6)-epoxy steroid having a 3-ketone blocked, for example, by an acetal group. Steroids having a 6-chlorine atom are prepared by known methods, for example by addition of the hydrochloric acid/dimethylformamide complex to a corresponding 5(6)-epoxy steroid having a 3-ketone blocked, for example, by an acetal group.

Steroids having a 16α-methyl are prepared by known methods, for example by addition of a methylmagnesium halide in the presence of a copper salt to a corresponding Δ$^{16}$-20-keto steroid which is itself obtained by dehydration of the corresponding 17-hydroxylated steroid. Steroids having a 16β-methyl radical are prepared by known methods, for example from a corresponding Δ$^{16}$-20-keto steroid which is treated with diazomethane, heated and then subjected to a hydrogenation reaction.

The compounds of formulae VII, VII', VII'' and VII''' are new products and the subject of the invention. The products of formulae VII, VII', VII'' and VII''', as well as the products of formula I$_A$ contrary to what is stated, cannot be obtained by the preparation described in Patent Application No. WO 8,701,706.

In the following examples there are described several preferred embodiments to illustrate the invention. However, it is to be understood that the invention is not intended to be limited to the specific embodiments.

EXAMPLE 1

N,N,N',N'-tetraethyl-6-(1-piperazinyl)-2,5-pyridinediamine

STEP A:

1-acetyl-4-[6-(diethylamino)-3-nitro-2-pyridyl]-piperazine

A solution of 51.22 g of N-acetylpiperazine in 200 ml of acetonitrile was added over 50 minutes at 0° C. to a mixture of 78 g of 2,6-dichloro-3-nitropyridine, 600 ml of acetonitrile and 66.3 g of potassium carbonate and after the mixture was allowed to return to room temperature, it was stirred for 75 minutes. The inorganic salts were filtered off and 180 ml of N,N-diethylamine and 76 g of potassium carbonate were added to the filtrate. The mixture was refluxed for 75 minutes and after cooling, the inorganic salts were filtered off. The filtrate was evaporated to dryness under reduced pressure and the 166.9 g residue were crystallized from 200 ml of ethyl acetate to obtain 87.4 g of the expected product melting at 120° C.

| IR Spectrum: (CHCl$_3$) | |
| --- | --- |
| C = 0 | 1637 cm$^{-1}$ |
| Conjugated system | 1593 cm$^{-1}$ |
| 1st NO$_2$ band | 1569 cm$^{-1}$–1510 cm$^{-1}$ |
| 2nd NO$_2$ band | 1346 or 1299 |

STEP B:

N,N,N',N'-tetraethyl-6-(1-piperazinyl)-2,5-pyridinediamine

A mixture of 70 g of the product of Step A, 1500 ml of methanol 61.5 ml of acetaldehyde and 10 g of activated charcoal containing 10% palladium was hydrogenated at a maximum pressure of 1250 mbar at 25° C. Approximately 20 liters of hydrogen were absorbed and the catalyst was filtered off. The filtrate was evaporated to dryness under reduced pressure and the 89.8 g of residue were taken up in 500 ml of n-propanol and 91.3 g of potassium hydroxide pellets. The mixture was refluxed for 3 hours and the cooled solution was poured into 1 liter of ice-cold water. The product was extracted with methylene chloride and the organic solution was washed with saturated sodium chloride solution, dried, filtered and concentrated to dryness under reduced pressure. The 58.9 g of residue were chromatographed on silica (eluant: methylene chloride-methanol-ammonia solution (95:5:0.5) to obtain 48.35 g of the expected product.

Analysis: C$_{17}$H$_{31}$N$_5$: Calculated: %C 66.84; %H 10.23; %N 22.93. Found: %C 66.9; %H 10.5; %N 22.6.

| IR Spectrum: (CHCl$_3$) | |
| --- | --- |
| C = C | 1596 cm$^{-1}$ |
| C = N | 1560 cm$^{-1}$ |
| Heteroaromatic | 1531 cm$^{-1}$ |
| | 1487 cm$^{-1}$ |

EXAMPLE 2

21-(4-[3,6-bis(diethylamino)-2-pyridyl]-1-piperazinyl)-16α-methyl-$\Delta^{1,4,9(11)}$-pregnatriene-3,20-dione 1.395 g of 21-iodo-16α-methyl-$\Delta^{1,4,9(11)}$-pregnatriene-3,20-dione (prepared by Patent No. WO 8,701,706), 40 ml of acetone, 1.88 g of the product of Example 1 and 0.9 g of potassium carbonate were mixed at room temperature and the mixture was stirred for 2 hours 30 minutes and filtered. The mixture was evaporated to dryness under reduced pressure and the 3.47 g of residue were chromatographed on silica (eluant: cyclohexane-ethyl acetate (7:3)) to obtain 1.4 g of the expected product with a specific rotation of $[\alpha]_D = +41°\pm2°5$ (c=0.4% in ethanol).

Analysis: $C_{39}H_{57}N_5O_2$: Calculated: %C 74.6; %H 9.15; %N 11.15. Found: %C 74.5; %H 9.4; %N 11.5.

| IR Spectrum: (CHCl₃) | |
|---|---|
| $\Delta^{1,4}$-3-one | 1663 cm$^{-1}$ |
| | 1624 cm$^{-1}$ |
| | 1604 cm$^{-1}$ |
| | 889 cm$^{-1}$ |
| Unconjugated ketone | 1714 cm$^{-1}$ |
| | 1701 cm$^{-1}$ |
| Heteroaromatic | 1594 cm$^{-1}$ |
| | 1561 cm$^{-1}$ |
| | 1486 cm$^{-1}$ |

PHARMACOLOGICAL STUDY

I) Antioxidant Activity

The antioxidant activity was tested for in vitro by the test of formation of malonyldialdehyde (MDA) which measures lipid peroxidation triggered: either a) non-enzymatically by ferrous sulfate in 1) brain homogenates, or 2) rat liver microsomes or b) enzymatically by NADPH and carbon tetrachloride in rat liver microsomes.

1.1: MDA formation was measured on 10-fold diluted (V/V) homogenates of brains of S-D rats (200 g) prepared in Krebs buffer pH 7.4 under the conditions described in J. Biol. Chem. Vol. 262 (1987) P. 10438-10440. 1 ml of homogenate was incubated for 60 minutes at 37° C. in the presence of 25 microliters of ethanol containing or not containing the test product, after the addition of 25 microliters of ferrous sulfate solution prepared immediately before use in water outgassed with argon (200 micromoles final). 0.25 ml of incubated mixture was withdrawn and 1.5 ml of 1% strength phosphoric acid, 0.25 ml of a solution containing 200 micromoles of deferoxamine (Desferal ®, Ciba Geigy) in water, 100 microliters of butylated hydroxytoluene (BHT) at a concentration of 8.7 mg/ml in ethanol and 0.5 ml of thiobarbituric acid (TBA) at a concentration of 0.6% in water were added. The mixture was heated to 100° C. for 45 minutes and cooled and 4 ml of n-butanol were added. The mixture was centrifuged for 15 minutes at 4000 rpm and the OD of the supernatant fraction was then read at 535 nm. The reaction blanks in the absence of Fe$^{++}$ were incubated under the same conditions and the percentage inhibition was calculated as follows:

$$\text{percentage inhibition} = \frac{\text{OD in the presence of product}}{\text{OD in the absence of product}}$$

The results are reported in the following Table.

| Concentration | $5 \times 10^{-4}$M | $1 \times 10^{-4}$M | $1 \times 10^{-5}$M |
|---|---|---|---|
| Percentage inhibition | | | |
| Product of Ex. 1 | 74.2 ± 3.8 | 67.4 ± 8.6 | 60.3 ± 9.1 |
| Product of Ex. 2 | 60.4 ± 4.4 | 55.6 ± 1.3 | 63.8 ± 4.3 |

1.2: MDA formation was measured on liver microsomes of S-D rats (200 g) prepared from the fraction sedimented at 100,000 g of a liver homogenate in a sucrose buffer, of which the fraction remaining insoluble at 100,000 g in 100 mM sodium pyrophosphate buffer pH 7.4 was used and which was homogenized in 100 mM sodium phosphate buffer pH 7.4 containing 20% of glycerol and was then stored at −80° C.

The microsomes were incubated for 15 minutes at 37° C. in 1 ml containing 35 mM Tris-HCl buffer/0.1M KCl pH 7.4, 1 mg of microsomal protein, 5 microliters of ethanol containing or not containing the test product and 250 microliters of ascorbate solution in the Tris buffer (0.5 mM final), after the addition of ferrous sulfate prepared immediately before use in the Tris buffer (6 micromoles final). The reaction was stopped by adding 2 ml of a 1M solution of trichloroacetic acid in 0.25M hydrochloric acid containing 0.4% of thiobarbituric acid. The mixture was heated to 85° C. for 25 minutes, cooled and centrifuged for 15 minutes at 3500 rpm. The OD of the supernatant fraction was then read at 535 nm and the reaction blanks in the absence of Fe$^{++}$ were performed at the same time. The percentage inhibition was calculated as above and the results are as follows:

| Concentration | $1 \times 10^{-5}$M | $5 \times 10^{-6}$M | $1 \times 10^{-6}$M |
|---|---|---|---|
| Percentage inhibition | | | |
| Product of Ex. 1 | 99.4 | 99.4 | 44.0 |
| Product of Ex. 2 | 99.8 | 99.5 | 42.0 ± 5 |

2: MDA formation was measured on liver microsomes of rats pretreated with phenobarbital (80 mg/kg by 3 i.p. injections), prepared as described above. The microsomes were incubated for 15 minutes at 37° C. in 1 ml containing 0.1M pH 7.4 phosphate buffer, 1 mg of microsomal protein, 5 microliters of ethanol containing or not containing the test product and 5 microliters of carbon tetrachloride (5.5 mM final) after the addition of 50 microliters of NADPH solution in the phosphate buffer (1 mM final). The reaction was stopped and the assay was then performed according to the conditions described above. The results were as follows:

| Concentration | $1 \times 10^{-5}$M | $51 \times 10^{-6}$M | $1 \times 10^{-6}$M |
|---|---|---|---|
| Percentage inhibition | | | |
| Product of Ex. 1 | 96 ± 1 | 93 ± 0.2 | 43 ± 3 |
| Product of Ex. 2 | 91 ± 1 | 88 ± 1 | 49 ± 1.5 |

II) Anti-Inflammatory Activity

The anti-inflammatory activity was assessed in vivo by measurement of the anti-oedematous activity by the test of arachidonic acid-induced plantar oedema described by Di Martino et al (Agents and Actions, 1987, 21 3/4 303). The experimental animals were Sprague-Dawley strain SPF male rats weighting 150 to 170 g (Iffa Credo).

The test was performed on groups of 8 male rats weighing 130 to 150 g, fasted for 16 hours. Arachidonic acid was injected under the plantar aponevrosis of one hindfoot at a dose of 0.2 mg in a volume of 0.1 ml. The volume of the foot was measured using a water plethysmometer before and 1 hour after the injection of arachidonic acid. The difference between these two volumes represented the degree of inflammation. The animals were treated with the test products or the vehicle alone at the same time as the injection of arachidonic acid. The test products were administered orally in a volume of 4 ml/kg after being suspended in 0.5% strength methyl-cellulose and all the experiments were carried out with dexamethasone administered orally at a dose of 0.5 mg/kg as reference product.

The results were expressed as a change in volume of the foot 1 hour after the injection of arachidonic acid (AA) in the absence or in the presence of the test product administered at different doses. Statistical interpretation of the results was performed according to Dunnett's test (* $p<0.05$-** $p<0.01$) or according to the Mann-Whitney test ($^{o}p<0.5$-$^{oo}p<0.01$). For each dose administered orally, the percentage of inhibition of the oedema by the test product was calculated relative to the control.

| | Dose mg/kg | Change in volume of the foot 1 hour after AA (cm$^3$) | % inhibition |
|---|---|---|---|
| Controls | 0 | 0.58 ± 0.04 | |
| Product of Example 2 | 0.5 | 0.32 ± 0.04** | −45 |
| | 1 | 0.32 ± 0.01** | −45 |
| Controls | 0 | 0.63 ± 0.01 | |
| Product of Example 1 | 20 | 0.33 ± 0.06** | −48 |

The test products have an anti-inflammatory activity at a low dose, especially the product of Example 2 which displayed high activity at a dose of 0.5 mg/kg and above. Under the same experimental conditions, dexamethasone induced a 30 to 40% inhibition of the oedema at a dose of 0.5 mg/kg.

Various modifications of the compounds and methods of the invention may be made without departing from the spirit or scope thereof and it should be understood that the invention is intended to be limited only as defined in the appended claims.

What we claim is:

1. A compound selected from the group consisting of the formula

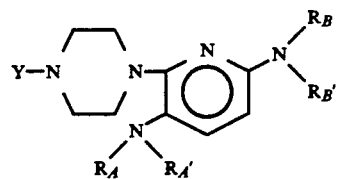

wherein $R_A$, $R_{A'}$, $R_B$ and $R_{B'}$ are individually selected from the group consisting of hydrogen and alkyl of 1 to 4 carbon atoms or $R_A$ and $R_{A'}$ or $R_B$ and $R_{B'}$ together with the nitrogen atom to which they are attached form pyrrolidine or piperidine optionally substituted with alkyl of 1 to 3 carbon atoms or pyrrole optionally substituted with alkyl of 1 to 3 carbon atoms and Y is hydrogen or

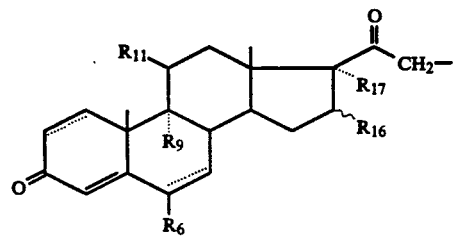

wherein $R_6$ is selected from the group consisting of hydrogen, —CH$_3$, —F and —Cl, $R_9$ and $R_{11}$ form a second bond at 9(11) or $R_9$ is hydrogen or —F and $R_{11}$ is hydrogen, —OH or =O, $R_{16}$ is —CH$_3$ or hydrogen, $R_{17}$ is hydrogen, —OH or acyloxy of an organic carboxylic acid, the dotted lines indicate the possible presence of a second bond at 1(2) and 6(7) positions and the wavy line indicates the α- and β-position for $R_{16}$, with proviso that when Y is is hydrogen, the compound is essentially free of the isomer compound of the formula

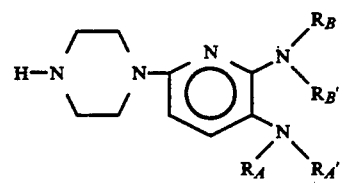

or its non-toxic, pharmaceutically acceptable addition salt.

2. A compound of claim 1 wherein Y is hydrogen.
3. A compound of claim 1 wherein Y is

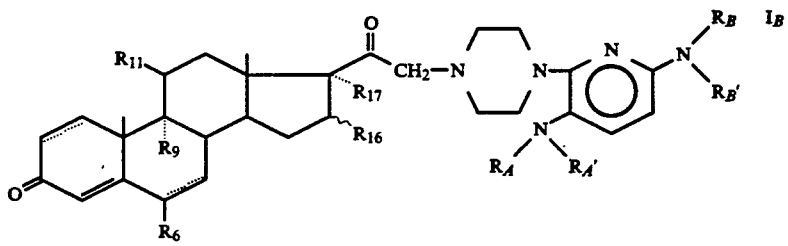

wherein $R_6$, $R_9$, $R_{11}$, $R_{17}$, $R_A$, $R_{A'}$, $R_B$ and $R_{B'}$, the dotted lines and the wavy line have the definitions of claim 1.

4. A compound of claim 3 wherein $R_6$ is hydrogen.

5. A compound of claim 3 wherein $R_9$ and $R_{11}$ form a second bond at the 9(11)-position.

6. A compound of claim 3 wherein $R_{16}$ is α-methyl.

7. A compound of claim 3 wherein $R_{17}$ is hydrogen.

8. A compound of claim 3 wherein the dotted line in the 1(2) position is a second bond.

9. A compound of claim 1 which is N,N,N',N'-tetraethyl-6-(1-piperazinyl)-2,5-pyridine-diamine or its non-toxic, pharmaceutically acceptable acid addition salts.

10. A compound of claim 1 is 21-(4-[3,6-bis(diethylamino)-2-pyridyl]-1-piperazinyl)-16α-methyl-$\Delta^{1,4,9(11)}$-pregnatriene-3,20-dione or its non-toxic, pharmaceutically acceptable acid addition salt.

11. An antioxidant composition comprising an antioxidantly effective amount of a compound of claim 1 and an inert pharmaceutical carrier.

12. A composition of claim 11 wherein the compound has the formula hydrogen.

13. A composition of claim 11 wherein Y is

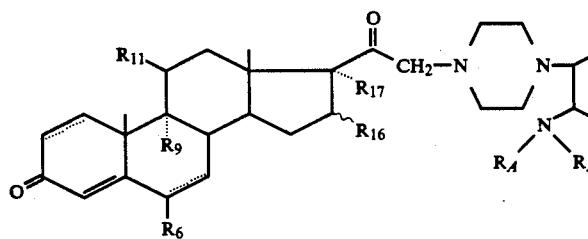

wherein $R_6$, $R_9$, $R_{11}$, $R_{17}$, $R_A$, $R_A$, $R_B$ and $R_B$, the dotted lines and the wavy line have the definitions of claim 1.

14. A composition of claim 11 wherein $R_6$ is hydrogen.

15. A composition of claim 11 wherein $R_9$ and $R_{11}$ form a second bond at the 9(11)-position.

16. A composition of claim 11 wherein $R_{16}$ is α-methyl.

17. A composition of claim 11 wherein $R_{17}$ is hydrogen.

18. A composition of claim 11 wherein the dotted line in the 1(2) position is a second bond.

19. A composition of claim 11 wherein the active ingredient is is N,N,N',N'-tetraethyl-6-(1-piperazinyl)-2,5-pyridine-diamine or its non-toxic, pharmaceutically acceptable acid addition salts.

20. A method of inducing antioxidant activity in warm-blooded animals comprising administering to warm-blooded animals an anti-oxidantly effective amount of a compound of claim 1.

21. A method of claim 20 wherein Y is hydrogen.

22. A method of claim 20 wherein the compound has the formula

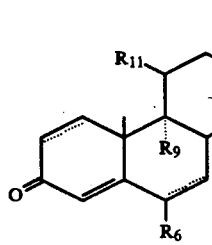 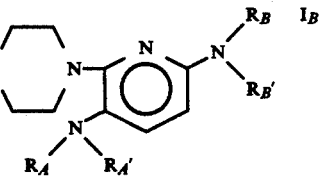

wherein $R_6$, $R_9$, $R_{11}$, $R_{17}$, $R_A$, $R_A$, $R_B$ and $R_B$, the dotted lines and the wavy line have the definitions of claim 1.

23. A method of claim 20 wherein $R_6$ is hydrogen.

24. A method of claim 20 wherein $R_9$ and $R_{11}$ form a second bond at the 9(11)-position.

25. A method of claim 20 wherein $R_{16}$ is -methyl.

26. A method of claim 20 wherein $R_{17}$ is hydrogen.

27. A method of claim 20 wherein the dotted line in the 1(2) position is a second bond.

28. A method of claim 20 wherein the active ingredient is is N,N,N',N'-tetraethyl-6-(1-piperazinyl)-2,5-pyridine-diamine or its non-toxic, pharmaceutically acceptable acid addition salts.

29. A method of claim 20 wherein the active ingredient is 21-(4-[3,6-bis(diethylamino)-2-pyridyl]-1-piperazinyl)-16α-methyl-$\Delta^{1,4,9(11)}$-pregnatriene-3,20-dione or its non-toxic pharmaceutically acceptable acid addition salts.

* * * * *

UNITED STATES PATENT AND TRADEMARK OFFICE
CERTIFICATE OF CORRECTION

PATENT NO. : 5,202,316
DATED : April 13, 1993
INVENTOR(S) : A. CLAUSSNER et al It is certified that error appears in the above-identified patent and that said Letters Patent is hereby corrected as shown below:

Column 12, line 51, change "Y is" to --the compound has the formula--

Column 13, line 31, change "Y is" to --the compound has the formula--

Signed and Sealed this

Sixth Day of September, 1994

BRUCE LEHMAN

Attest:

*Attesting Officer*                    *Commissioner of Patents and Trademarks*